United States Patent [19]

Beskin

[11] Patent Number: 4,747,417

[45] Date of Patent: May 31, 1988

[54] SPRAYABLE COMPOSITION TO PREVENT SMOKING

[75] Inventor: Michael D. Beskin, Riverdale, N.Y.

[73] Assignee: Besco Laboratory Inc., New York, N.Y.

[21] Appl. No.: 774,464

[22] Filed: Sep. 10, 1985

[51] Int. Cl.$^4$ .............................................. A24F 47/00
[52] U.S. Cl. .................................... 131/270; 131/329
[58] Field of Search ................................ 131/270, 329

[56] References Cited

FOREIGN PATENT DOCUMENTS 0086180 8/1983 European Pat. Off. ............. 131/270
2747500 4/1979 Fed. Rep. of Germany ...... 131/270

*Primary Examiner*—V. Millin
*Attorney, Agent, or Firm*—Karl F. Ross; Herbert Dubno

[57] ABSTRACT

A new composition is disclosed for the prevention of smoking which consists essentially of:
  (a) 2 to 4 parts/weight of a solution of silver acetate in distilled water or deionized water at a concentration of 1.5 to 7.5 g/l; and
  (b) 1 part/weight of a solution of ethanol of a pharmaceutical grade in which is dissolved an effective amount of a flavoring agent in the ethanol. Preferably, the composition is applied by spraying. The composition is made by a process which involves stirring of a mixture of water and the silver acetate for a prolonged period and combining the silver acetate solution with a solution of a flavoring agent in ethanol. When sprayed into the mouth, the resulting composition gives an unpleasant metallic taste discouraging smoking.

6 Claims, No Drawings

SPRAYABLE COMPOSITION TO PREVENT SMOKING

FIELD OF THE INVENTION

This invention relates to a sprayable composition to discourage smokers from continuing to smoke as well as to a process for preparing said compositions.

BACKGROUND OF THE INVENTION

There is little doubt today that the smoking of tobacco, especially in cigarette form, is harmful to the health of the individual. Statistically significant evidence has been assembled over the past thirty years showing a direct correlation between smoking and lung cancer, smoking and coronary disease, and smoking and respiratory disease. Many smokers today only wish that their smoking habit could be broken, but somehow lack the will-power to permanently stay away from tobacco.

Actually smoking is addictive and involves both physical addiction and mental addiction. The physical addiction takes place because the smoker physically craves the nicotine contained in the tobacco. The mental addiction is stimulated principally by what occurs in the day-to-day life of the individual smoker. For instance, if others in the same environment smoke, social pressure may be put on said individual to smoke as well.

There are several products on the market used to discourage smokers from continuing the habit. Some of the products have achieved a limited measure of success, but as yet no one product has been really satisfactory to permanently discourage smoking in a large percentage of the smoking population. One such product on the market contains silver acetate in the form of a chewing gum. The product is effective because the silver acetate reacts with the nicotine in the tobacco to effect the mucous membranes of the mouth in such a way that when the tobacco comes into contact with the silver acetate, a nasty, disagreeable metallic taste is produced. Because of this disagreeable taste, smoking becomes less desirable and the smoker is discouraged into eliminating or at least into reducing the smoking habit.

One of the drawbacks to the use of the chewing gum containing the silver acetate is the fact that constant chewing must take place for a number of hours in order to achieve the desired effect. A smoker can simply throw out the chewing gum once the bad taste develops in his mouth and only minutes later "light up" once again. Furthermore in many business and social situations, chewing gum is not practical. Finally smokers who have dental work may not be able to use a chewing gum to break the smoking habit.

OBJECTS OF THE INVENTION

It is an object of the invention to provide a composition to discourage smoking and which can be easily used by anyone.

It is a further object of the invention to provide a composition which will remain effective to discourage smoking for a prolonged time period.

SUMMARY OF THE INVENTION

These objects and others which will become apparent hereinafter are attained, in accordance with the present invention, which provides a sprayable composition to discourage smokers from continuing to smoke, and which contains silver acetate as an active ingredient. The silver acetate reacts with the nicotine to form the disagreeable metallic taste that will last 4 to 5 hours. The composition may be applied 4 times a day and in the case of very heavy smokers up to 8 times a day.

The new composition contains 2 to 4 parts by weight of a solution of silver acetate in distilled water or deionized water at a concentration of 1.5 to 7.5 g/l and 1 part by weight of a solution of ethanol of a pharmaceutical grade in which is dissolved an effective amount of a flavoring agent, and an amount of polysorbate 80 effective to solubilize the flavoring agent in the ethanol.

Generally the flavoring agent is included in an amount of 1 to 5% of the ethanol, preferably about 3%. The amount of polysorbate 80 employed to dissolve the flavoring agent in the ethanol ranges from 2 to 10% by weight of the ethanol, preferably about 6%.

The flavoring agent is an aromatic oil such as peppermint oil, spearmint oil, wintergreen oil, oil of cloves or oil of cinnamon The new compositions contain no synthetic sweeteners as flavoring agents, such as sorbitol or saccharin. It has been found that the synthetic sweeteners adversely effect the solubility of the silver acetate salt in the aqueous solution once the ethanolic solution is added thereto. Thus the use of synthetic sweeteners is to be avoided.

The composition is prepared starting with distilled or deionized water. It is important to use distilled or deionized water because normal tap water usually contains a significant amount of halide ions which have the ability to render insoluble the silver in the silver acetate in the form of a very insoluble silver halide precipitate.

The silver acetate itself has a fairly low solubility in water (1.02g/100 ml) and so the salt is added very slowly to the distilled or deionized water over a 24 hour period under continuous stirring to form a solution containing 1.5 to 7.5 g/l. The vessel containing the distilled or deionized water must be wrapped with an opaque material to protect the resulting mixture from light as silver acetate is highly sensitive to light.

After 24 hours of stirring the silver acetate is dissolved. In the meantime in a separate vessel polysorbate 80 and a flavoring agent such as peppermint oil, spearmint oil, wintergreen oil, oil of cloves or oil of cinnamon are added to the ethanol of pharmaceutical quality. The resulting ethanol solution is added in small quantities, and with stirring, to the solution of silver acetate in distilled or deionized water. The ethanol solution must be added bit-by-bit (e.g. 1% of the total solution at a time) over a 24 hour period in order to prevent the poorly water-soluble silver acetate from coming out of the solution. Preferably 10 to 15 minutes should elapse before the time that one portion of ethanol has been added and the next portion is to be added.

The resulting solution may then be diluted by 1 to 100% with distilled or deionized water, ready for packaging, preferably in the form of a spray. The product is packaged in a nonpropellant dispenser, i.e. a pump dispenser having a spray nozzle as in the case of a conventional pump spray for bad breath. The pump meters 0.0004 to 0.0005, preferably, in a very fine mist per spray.

The product is orally applied by the smoker, preferably by spraying each time, 4 sprays in the same way as a breath freshener would be applied. There is no need for the user to rinse his mouth. The composition will not react with food or drink. But as soon as the smoker begins to use tobacco, the smoker will experience the unfamiliar, objectionable metallic taste resulting from a chemical reaction between the silver acetate in the composition and the nicotine in the tobacco.

Preferably to supply a long lasting effect to the smoker, usage of the composition should begin the first thing in the morning, right after brushing the teeth.

EXAMPLE (a) To an 18.9 liter (5 gallon) container, 14.7 liters (3.9 gallons) of distilled or deionized water are added, followed by 6.27 g (2.34 av.oz.) of silver acetate. The container is wrapped with an opaque material to protect the mixture from light. The mixture is then stirred for 24 hours to dissolve the silver acetate.

(b) Into 3.8 liters (1 gallon) of pharmaceutical grade ethanol are dissolved 227 ml (0.48 pints) of polysorbate 80 (Tween) and 114 ml (0.24 pints) of peppermint oil. The resulting solution is added in several small portions and with stirring, to the silver acetate solution prepared in part (a).

(c) The mixture obtained in step (b) is then diluted to a total volume of 18.9 liters (5 gallons) with distilled or deionized water.

What is claimed is:

1. A pump bottle containing a sprayable composition for the prevention of smoking which consists of:
   (a) 2 to 4 parts by weight of a solution of silver acetate in distilled water or deionized water at a concentration of 1.5 to 7.5 g/l; and
   (b) 1 part by weight of a solution of ethanol of a pharmaceutical grade in which is dissolved an effective amount of a flavoring agent selected from the group which consists of peppermint oil, spearmint oil, wintergreen oil, cloves oil and cinnamon oil, and an amount of polysorbate 80 effective to solubilize the flavoring agent in the ethanol, and 1% to 100% distilled water or deionized water based on the weight of the composition.

2. A process for making a composition for the prevention of smoking which comprises the steps of:
   (a) forming a sprayable composition by mixing silver acetate and distilled or deionized water to provide a mixture having a concentration of 1.5 to 7.5 g/l of silver acetate;
   (b) stirring the mixture for about 24 hours to dissolve the silver acetate;
   (c) dissolving in pharmaceutical grade ethanol an effective amount of a flavoring agent selected from the group which consists of peppermint oil, spearmint, wintergreen oil, oil of cloves and oil of cinnamon and an amount of polysorbate 80 effective to dissolve the flavoring agent in the ethanol;
   (d) adding the ethanol solution formed in step (c) to the silver acetate solution formed in step (b) in small portions, and with stirring to form a mixture constituted by 2 to 4 parts by weight of silver acetate solution to 1 part by weight of ethanol solution; and
   (e) packaging said composition in a pump dispenser and with a spraying means so as to be in sprayable form.

3. The process defined in claim 2, wherein in step (d), the ethanol solution is added to the silver acetate solution over a 24 hour period, about 1% every 15 minutes.

4. The process defined in claim 2 further comprising the step of diluting the composition formed in step (d) by the addition of 1% to 100% distilled water or deionized water based on the weight of the composition.

5. A method of preventing an individual from smoking tobacco which comprises the step of orally administering to said individual by pump spraying into the mouth an amount of the composition defined in claim 1 effective to form a complex with the nicotine contained in the tobacco and the silver acetate in the composition, wherein said complex has an unpleasant metallic taste, thereby discouraging the smoker from continuing to smoke.

6. The method defined in claim 5 wherein the composition is applied 4 sprays at a time, 4 times a day.

* * * * *